United States Patent [19]

Goldenberg et al.

[11] Patent Number: 4,474,766

[45] Date of Patent: Oct. 2, 1984

[54] ANTI-INFLAMMATORY/ANALGESIC COMBINATION OF CYCLO-(N-METHYL-ALA-TYR-D-TRP-LYS-VAL-PHE) AND A SELECTED NON-STEROIDAL ANTI-INFLAMMATORY DRUG (NSAID)

[75] Inventors: Marvin M. Goldenberg, Westfield; Doris L. Keller, Edison, both of N.J.

[73] Assignee: Merck & Co., Inc., Rahway, N.J.

[21] Appl. No.: 507,849

[22] Filed: Jun. 27, 1983

[51] Int. Cl.³ .............................................. A61K 37/00
[52] U.S. Cl. ................................................... 424/177
[58] Field of Search ................... 260/112.5 S; 424/177

[56] References Cited

U.S. PATENT DOCUMENTS 4,310,518  1/1982  Freidinger et al. .......... 260/112.5 S

OTHER PUBLICATIONS

Chem. Abstr. vol. 98, 1983, 752v.
Chem. Abstr. vol. 94, 1981, 76964d.
Chem. Abstr. vol. 91, 1979, 117810j.
Chem. Abstr. vol. 87, 1977, 63200g.
Chem. Abstr. vol. 89, (1978), 53800e.
Chem. Abstr. vol. 98, (1983), 84216j.
Biol. Abstr. (1978), 64207, vol. 65.

*Primary Examiner*—Delbert R. Phillips
*Attorney, Agent, or Firm*—Theresa Y. Cheng

[57] ABSTRACT

Combinations of cyclo-(N-methyl-Ala-Tyr-D-Trp-Lys-Val-Phe) and a NSAID have been found to exhibit much lower gastric lesions or ulcers than normally associated with NSAIDs and are thereby clinically useful in long-term therapy for patients suffering from chronic rheumatoid arthritis or osteoarthritis.

12 Claims, No Drawings

ANTI-INFLAMMATORY/ANALGESIC COMBINATION OF CYCLO-(N-METHYL-ALA-TYR-D-TRP-LYS-VAL-PHE) AND A SELECTED NON-STEROIDAL ANTI-INFLAMMATORY DRUG (NSAID)

BACKGROUND OF THE INVENTION

This invention relates to novel pharmaceutical combinations comprising cyclo-(N-methyl-Ala-Tyr-D-Trp-Lys-Val-Phe) and one or more non-steroidal anti-inflammatory/analgesic drugs (NSAID) particularly indomethacin, ibuprofen, diclofenac, and naproxen. Unexpectedly, these novel combinations exhibit remarkable ability to prevent gastrointestinal intolerance that is normally associated with NSAIDs. They are therefore superior to the separate NSAIDs in the treatment of chronic rheumatoid arthritis or osteroarthritis.

Non-narcotic analgesics, also known as non-steroidal anti-inflammatory drugs (NSAID), are widely administered orally in the treatment of inflammation and mild to moderate pain. Within this class, the compounds vary widely in their chemical structure and in their biological profiles as analgesics, anti-inflammatory agents and antipyretic agents. Aspirin, acetaminophen and phenacetin have long been among the most commonly used members of this group; more recently, however, a large number of alternative non-narcotic agents offering a variety of advantages over the earlier drugs have been developed. Addiction to these drugs is not generally a problem with their continuous use in the treatment of pain, acute or chronic inflammatory diseases, (notably, rheumatoid arthritis, osteoarthritis, and dysmenorrhea). However, these new drugs generally have a higher potential for adverse side-effects particularly those related to gastric ulcers. Among the newer compounds in the non-narcotic analgesic/ non-steroidal anti-inflammatory group are compounds such as indomethacin (INDOCIN), diflunisal (DOLOBID), zomepirac sodium (ZOMAX), ibuprofen (MOTRIN), naproxen (NAPROSYN), fenoprofen (NALFON), piroxicam (FELDENE), flurbiprofen, mefenamic acid (PONSTEL) and sulindac (CLINORIL). See *Physician's Desk Reference*, 35th edition, 1981, and *The Merck Index*, 9th edition, Merck & Co., Rahway, N.J. (1976), for information on specific non-steroidal anti-inflammatory agents.

Cyclo-(N-methyl-Ala-Tyr-D-Trp-Lys-Val-Phe) is a known compound being described in U.S. Pat. No. 4,310,518 issued to Roger M. Freidinger et al. on Jan. 12, 1982. The compound is a somatostatin analog having the structural formula (A):

N—Me—Ala—Tyr—D-Trp (A)
|                         |
Phe—Val——Lys wherein Ala represents alanine, Tyr represents L-tyrosine, D-Trp represents D-tryptophan, Lys represents L-lysine, Val represents L-valine, and Phe represents L-phenylalanine. The compound inhibits the release of glucagon, growth hormone and insulin. It may also inhibit the release of gastric acid secretions and is therefore suggested by the patent as useful in the treatment of peptic ulcers.

Accordingly, it is the object of the present invention to provide a novel combination of cyclo-(N-methyl-Ala-Tyr-D-Trp-Lys-Val-Phe) and one or more NSAIDs for use in the treatment of chronic rheumatoid arthritis or osteoarthritis devoid of undesirable gastrointestinal hemmorrhage or lesions normally associated with NSAIDs.

Another object of the invention is to provide pharmaceutical compositions for the administration of these combinations.

Still a further object of this invention is to provide an improved method of treating pain and inflammatory conditions by administering a sufficient amount of the novel combinations in a mammalian species in need of such treatment.

DETAILED DESCRIPTION OF THE INVENTION

This invention relates to a novel combination which enables long-term administration of one or more NSAIDs to patients suffering from chronic arthritis at lower risks of gastointestinal intolerance than possible from any of the NSAIDs used alone.

The components of the combination are (A) 0.005 to 10 parts preferably 0.01 to 5 by weight of cyclo-(N-methyl-Ala-Tyr-D-Trp-Lys-Val-Phe); and (B) One hundred parts by weight of one or more non-steroidal anti-inflammatory drugs (NSAID) comprising compounds which can be categorized into five groups:

(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group. Structural formulae for representative group members are set forth below:

| PROPIONIC ACID DERIVATIVES | |
|---|---|
| ibuprofen | 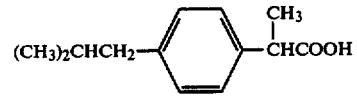 |
| naproxen | 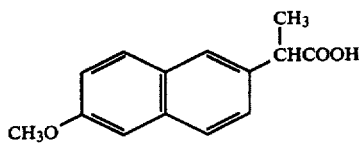 |
| flurbiprofen | 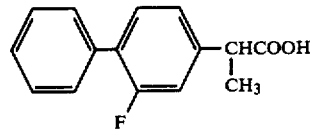 |
| fenbufen | 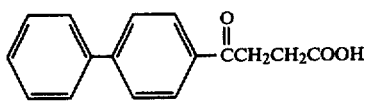 |

| PROPIONIC ACID DERIVATIVES | |
|---|---|
| fenoprofen | 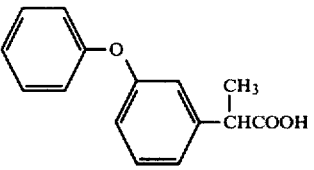 |
| ibuprofen aluminum | 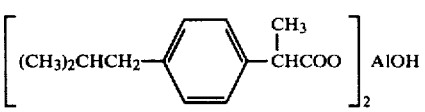 |
| indoprofen | 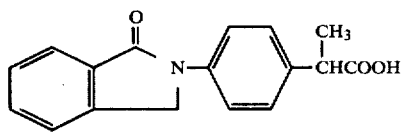 |
| ketoprofen | 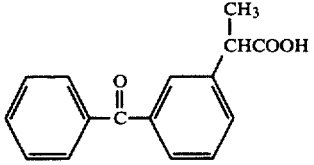 |
| fluprofen | 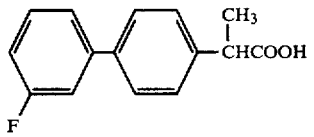 |
| bucloxic acid | 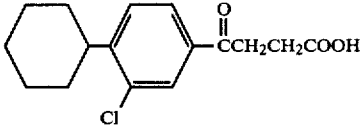 |

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, sulindac, tolmetin, zomepirac, diclofenac, tenclofenac, alclofenac, ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group. Structural formulas for representative group members are set forth below:

| ACETIC ACID DERIVATIVES | |
|---|---|
| zomepirac | 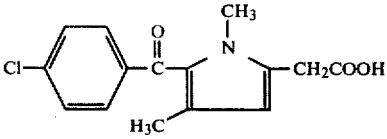 |
| tolmetin | 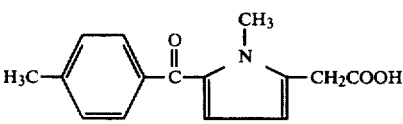 |
| sulindac | 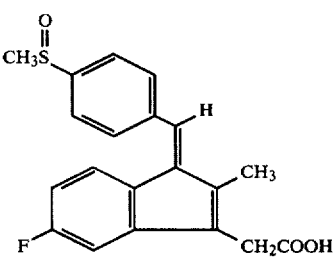 |
| indomethacin | 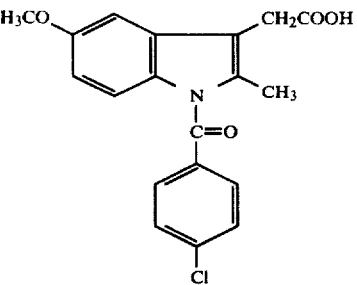 |
| diclofenac | 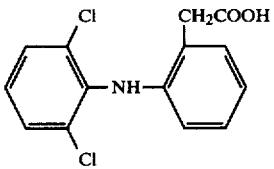 |
| alclofenac | 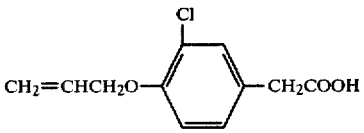 |
| fenclozic acid | 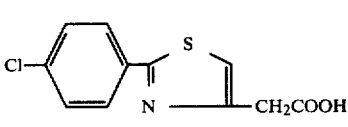 |
| ibufenac | 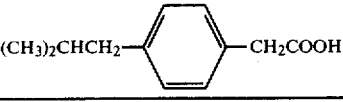 |

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group. Structural formulas for representative group members are set forth below:

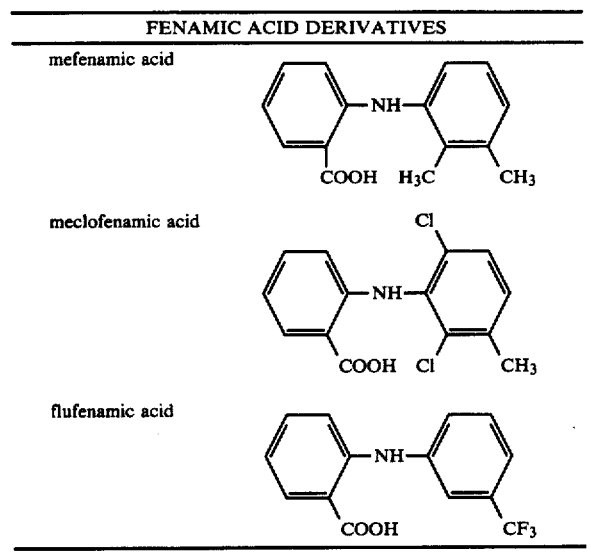

FENAMIC ACID DERIVATIVES
mefenamic acid
meclofenamic acid
flufenamic acid

Thus, "fenamic acid derivatives" as defined herein are non-narcotic analgesics/non-steroidal anti-inflammatory drugs which contain the basic structure:

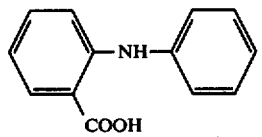

which can bear a variety of substituents and in which the free —COOH group can be in the form of a pharmaceutically acceptable salt group, e.g., $-COO^-Na^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

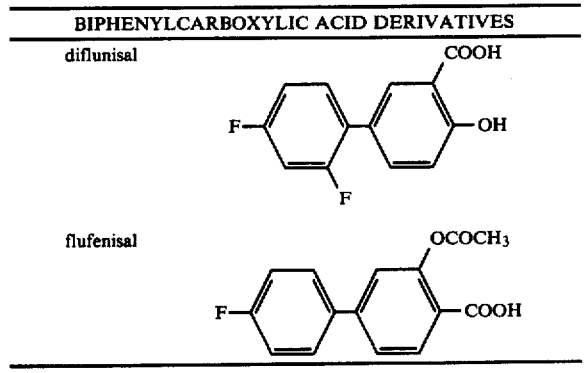

BIPHENYLCARBOXYLIC ACID DERIVATIVES
diflunisal
flufenisal

Thus, "biphenylcarboxylic acid derivatives" as defined herein are non-narcotic analgesics/non-steroidal anti-inflammatory drugs which contain the basic structure:

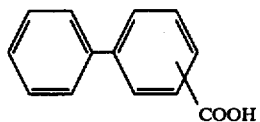

which can bear a variety of substituents and in which the free —COOH group can be in the form of a pharmaceutically acceptable salt group, e.g., $-COO^-Na^+$.

The oxicams which can be used in the present invention comprise: piroxicam, sudoxicam, isoxicam and 4-hydroxyl-1,2-benzothiazine 1 1-dioxide 4-(N-phenyl)-carboxamide. Structurally related oxicams having similar analgesic and anti-inflammatory properties are also intended to be encompassed by this group. Representative members are depicted below:

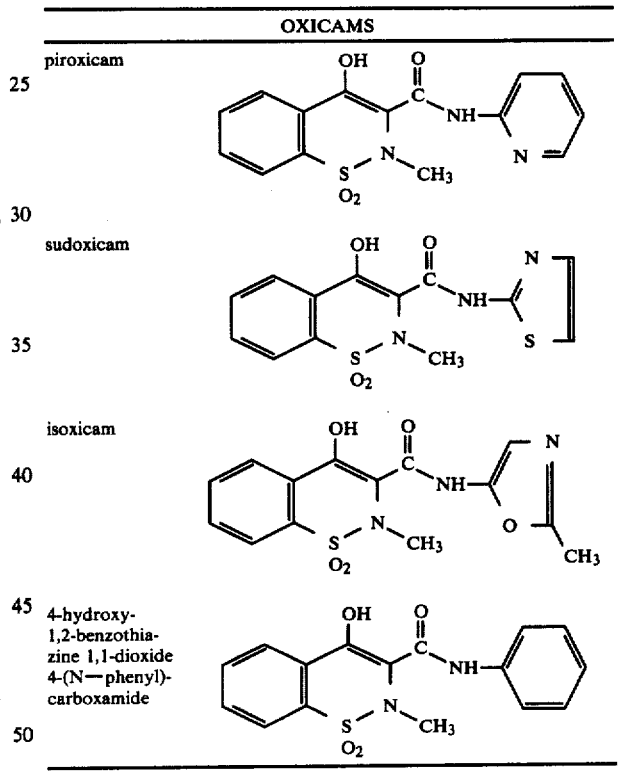

OXICAMS
piroxicam
sudoxicam
isoxicam
4-hydroxy-1,2-benzothiazine 1,1-dioxide 4-(N—phenyl)-carboxamide Thus, "oxicams" as defined herein are non-narcotic analgesics/non-steroidal anti-inflammatory drugs which have the general formula:

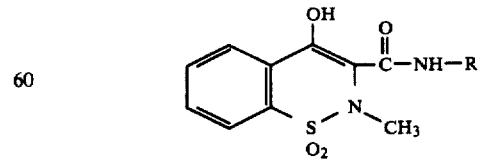

wherein R is an aryl or heteroaryl ring system.

When a selected NSAID, for example, indomethacin, is combined with cyclo-(N-methyl-Ala-Tyr-D-Trp-Lys-Val-Phe) according to the present invention, the following results are obtained from the well-established gastric ulcer assay in the Sprague-Dawley male rat is described below:

Protocol: NSAID-Induced Ulcers in the Sprague-Dawley Rat

Twenty-four (24) hour fasted, male, Sprague-Dawley rats, 130 to 150 gms. each, are randomized into groups for assay. The animals are housed to wire-bottom cages without bedding and allowed free-access to water throughout the fasting and experimental periods. Ulcers are then induced by the peroral administration of NSAID at dose levels predetermined to provoke a similar number of ulcers within 4 hours of additional fasting*. Each NSAID is prepared in 0.5% methyl cellulose vehicle and given at a volume of 10 ml/kg rounded to the nearest 0.1 ml. Either 0.5% methylcellulose vehicle or compound A is co-administered perorally with the NSAID bringing the total volume to 20 ml/kg rounded to the nearest 0.2 ml.

*For example: Indomethacin-20 mg/kg; Naproxen-50 mg/kg; Ibuprofen-100 mg/kg; Diclofenac-75 mg/kg.

Four (4) hours after the administration of NSAID+vehicle, or NSAID+compound A, the animals are sacrificed by $CO_2$ inhalation, the stomachs removed, excised along the inner curvature, washed carefully with cool tap water and placed in 0.9% saline. When all groups have been processed, the mucosal region of the stomachs are examined under a magnifying lens and scored according to the total number of lesions present. Group scores represent the mean score of animals in that group. P values are determined by Student's "t" test, comparing the ulcer scores of individual rats given NSAID+compound A to those dosed with NSAID+vehicle only.

| DRUG | Dose mg/kg p.o. | N | No. of Gastric Ulcers M ± S.E.M. | Inhibition of Gastric Ulcers |
|---|---|---|---|---|
| I. Combination of Indomethacin and Cyclo-(N—Methyl-Ala—Tyr—D-Trp—Lys—Val—Phe) (Compound A)* | | | | |
| Indomethacin + Vehicle | 20 | 15 | 18.1 ± 1.6 | 0 |
| Indomethacin + Compound A | 20 0.01 | 11 | 18.6 ± 4.4 | 0 |
| Indomethacin + Compound A | 20 0.01 | 11 | 9.0 ± 1.9 | 50.3** |
| Indomethacin + Compound A | 20 0.1 | 11 | 3.0 ± 1.3 | 83.4** |
| Compound A | 1.0 | | | |

*Administered simultaneously with Indomethacin

| II. Combination of Naproxen and Cyclo-(N—Methyl-Ala—Tyr—D-Trp—Lys—Val—Phe) (Compound A)* | | | | |
|---|---|---|---|---|
| Naproxen + Vehicle | 50 | 10 | 15.5 ± 1.7 | 0 |
| Naproxen + Compound A | 50 0.01 | 6 | 14.0 ± 3.0 | 0 |
| Naproxen + Compound A | 50 0.01 | 6 | 5.0 ± 2.5 | 67.7** |
| Naproxen + Compound A | 50 0.1 | 6 | 2.5 ± 1.4 | 83.9** |
| Compound A | 1.0 | | | |

*Administered simultaneously with Naproxen

| III. Combination of Ibuprofen and Cyclo-(N—Methyl-Ala—Tyr—D-Trp—Lys—Val—Phe) (Compound A)* | | | | |
|---|---|---|---|---|
| Ibuprofen | 100 | 20 | 12.9 ± 1.6 | 0 |
| Ibuprofen + Vehicle | 100 | 12 | 8.2 ± 1.0 | 36.4** |
| Ibuprofen + Compound A | 100 0.01 | 12 | 1.6 ± 0.6 | 87.6** |
| Ibuprofen + Compound A | 100 0.1 | 12 | 1.0 ± 0.5 | 92.3** |
| Compound A | 1.0 | | | |

*Administered simultaneously with Ibuprofen

| IV. Combination of Diclofenac and Cyclo-(N—Methyl-Ala—Tyr—D-Trp—Lys—Val—Phe) (Compound A)* | | | | |
|---|---|---|---|---|
| Diclofenac + Vehicle | 75 | 20 | 14.0 ± 1.6 | 0 |
| Diclofenac + Compound A | 75 0.01 | 12 | 18.7 ± 2.0 | 0 |
| Diclofenac + Compound A | 75 0.01 | 12 | 7.3 ± 2.3 | 47.9** |
| Diclofenac + Compound A | 75 0.1 | 12 | 0.1 ± 0.1 | 99.3** |
| Compound A | 1.0 | | | |

*Administered simultaneously with Diclofenac
**Statistically significantly different from control; $p = <0.05$ For treatment of inflammation, fever or pain, the combinations of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the combinations of the present invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manfacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical composition of the present invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as solvents or suspending media. For this purpose any bland fixed oil may be employed including synthetic mono- or diglycerides. In addition, fatty acids such as oleic acid find use in the preparation of injectables.

The combinations of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

The precise amount of non-narcotic analgesic/non-steroidal anti-inflammatory drug for use in the present compositions will vary depending, for example, on the specific drug chosen, the condition for which the drug is administered and the size and kind of the mammal. Generally speaking, the selected NSAID can be employed in any amount known to be an effective analgesic or anti-inflammatory amount, as well as at doses one-fifth to one-third lower than the usual amounts.

For humans, typical effective analgesic/anti-inflammatory amounts of preferred NSAIDs for use in unit dose compositions of the invention are about 50 to 150 mg indomethacin, about 125 to 1000 mg diflunisal, about 25 to 100 mg zomepirac sodium, about 400 to 2400 mg ibuprofen, about 250 to mg naproxen, about 25 to 150 mg flurbiprofen, about 50 to 400 mg fenoprofen, about 10 to 20 mg piroxicam, about 200 to 400 mg mefenamic acid, about 200 to 800 mg fenbufen or about 50 to 150 mg ketoprofen; however, greater amounts can be employed if desired. The amount of cyclo-(N-methyl-Ala-Tyr-D-Trp-Lys-Val-Phe) in the combination will be an amount sufficient to prevent gastrointestinal intolerance. However, certain NSAIDs are particularly long-acting and need be administered less frequently than the usual every 4 to 6 hours; for example, diflunisal and naproxen are typically administered only twice daily and piroxicam only once a day. When such long-acting drugs are employed, it is often necessary to include an additional amount of cyclo-(N-methyl-Ala-Tyr-D-Trp-Lys-Val-Phe) in the composition in sustained release form; thus, the composition will typically contain from about 0.5 to about 100 mg for immediate release and one (or possibly more) additional dose of about 0.5 to about 100 mg for sustained release. The daily dose in humans will vary with the selected NSAID, and may of course be as low as the amount contained in a single unit dose as set forth above.

What is claimed is:

1. A pharmaceutical combination for pain and antiinflammatory management in the treatment of chronic arthritis comprising a therapeutically effective amount of a non-steroidal anti-inflamnatory drug (NSAID) or a pharmaceutically acceptable non-toxic salt thereof and cyclo-(N-methyl-Ala-Tyr-D-Trp-Lys-Val-Phe) in an amount sufficient to prevent gastrointestinal intolerance.

2. The pharmaceutical combination according to claim 1 wherein the weight ratio of one or more NSAIDs to cyclo-(N-methyl-Ala-Tyr-D-Trp-Lys-Val-Phe) is from about 100 parts to about 0.005–10 parts.

3. The pharmaceutical combination according to claim 1 wherein the weight ratio of one or more NSAIDs to cyclo-(N-methyl-Ala-Tyr-D-Trp-Lys-Val-Phe) is from about 100 parts to about 0.01 to 5 parts.

4. The pharmaceutical combination according to claim 1 wherein the NSAID is
  (a) indomethacin;
  (b) ibuprofen;
  (c) naproxen; or
  (d) diclofenac.

5. A method for managing pain and inflammation in the treatment of chronic arthritis comprising administration to a patient in need of such treatment a therapeutically effective amount of a NSAID or a pharmaceutically acceptable non-toxic salt thereof and cyclo-(N-methyl-Ala-Tyr-D-Trp-Lys-Val-Phe) in an amount sufficient to prevent gastrointestinal intolerance.

6. The method according to claim 1 wherein the weight ratio of one or more NSAIDs to cyclo-(N-methyl-Ala-Tyr-D-Trp-Lys-Val-Phe) is from about 100 parts to about 0.005–10 parts.

7. The method according to claim 6 wherein the weight ratio of one or more NSAIDs to cyclo-(N-methyl-Ala-Tyr-D-Trp-Lys-Val-Phe) is from about 100 parts to about 0.01 to 5 parts.

8. The method according to claim 6 wherein the NSAID is
  (a) indomethacin;
  (b) ibuprofen;
  (c) naproxen; or
  (d) diclofenac.

9. A pharmaceutical composition for managing inflammation and pain in the treatment of chronic arthritis comprising a therapeutically effective amoutn of NSAID of a pharmaceutically acceptable non-toxic salt thereof; cyclo-(N-methyl-Ala-Tyr-D-Trp-Lys-Val-Phe) in an amount sufficient to prevent gastrointestinal intolerance; and a pharmaceutically acceptable carrier.

10. The composition of claim 1 wherein the weight ratio of one or more NSAIDs to cyclo-(N-methyl-Ala-Tyr-D-Trp-Lys-Val-Phe) is from about 100 parts to about 0.005–10 parts.

11. The composition of claim 1 wherein the weight ratio of one or more NSAIDs to cyclo-(N-methyl-Ala-Tyr-D-Trp-Lys-Val-Phe) is from about 100 parts to about 0.01 to 5 parts.

12. The composition of claim 11 wherein the NSAID is
  (a) indomethacin;
  (b) ibuprofen;
  (c) naproxen; or
  (d) diclofenac.

* * * * *